(12) United States Patent
Lanin et al.

(10) Patent No.: US 8,702,659 B2
(45) Date of Patent: Apr. 22, 2014

(54) DRUG DELIVERY DEVICE

(75) Inventors: Irina Lanin, Frankfurt am Main (DE); Bernhard Forys, Frankfurt am Main (DE); Alastair Clarke, Nantwich (GB); Matthew Ekman, Macclesfield (GB); Kirsten Goode, Frankfurt am Main (DE); Michael Heald, Crewe (GB); John Hiles, South Wirral (GB); Chris Smith, Holmes Chapel (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 30 days.

(21) Appl. No.: 13/202,440

(22) PCT Filed: Mar. 4, 2010

(86) PCT No.: PCT/EP2010/052790
§ 371 (c)(1),
(2), (4) Date: Jan. 6, 2012

(87) PCT Pub. No.: WO2010/100245
PCT Pub. Date: Sep. 10, 2010

(65) Prior Publication Data
US 2012/0095414 A1    Apr. 19, 2012

(30) Foreign Application Priority Data
Mar. 6, 2009  (EP) .................................. 09003279

(51) Int. Cl.
*A61M 5/00* (2006.01)
*A61M 5/32* (2006.01)

(52) U.S. Cl.
USPC .......................................... 604/187; 604/196

(58) Field of Classification Search
USPC .......................... 604/187, 195–196, 110, 218
See application file for complete search history.

(56) References Cited

U.S. PATENT DOCUMENTS 5,722,960 A    3/1998  Duplan et al.
2007/0250003 A1  10/2007  Bare et al.

FOREIGN PATENT DOCUMENTS

GB    2341804    3/2000
WO    2009/003234    1/2009

OTHER PUBLICATIONS

European Search Report for EP Application No. 09003279, dated Jul. 22, 2009.
International Search Report and Written Opinion for Int. App. No. PCT/EP2010/052790, mailed Jun. 11, 2010.

*Primary Examiner* — Manuel Mendez
*Assistant Examiner* — Rebecca E Eisenberg
(74) *Attorney, Agent, or Firm* — McDonnell Boehnen Hulbert & Berghoff LLP

(57) ABSTRACT

Drug delivery device, comprising a body unit having a first opening and a second opening, a plunger arranged such that its distal end is positioned inside the body unit, wherein the plunger is moveable in the distal direction with respect to the body unit, a needle assembly, with a proximal end and a distal end comprising a needle, wherein the proximal end of the needle assembly and the distal end of the plunger are configured such that they can get into an adhesion connection.

17 Claims, 5 Drawing Sheets

DRUG DELIVERY DEVICE

CROSS REFERENCE TO RELATED APPLICATIONS

The present application is a U.S. National Phase Application pursuant to 35 U.S.C. §371 of International Application No. PCT/EP2010/052790 filed Mar. 4, 2010, which claims priority to EP Patent Application No. 09003279.8 filed on Mar. 6, 2009. The entire disclosure contents of these applications are herewith incorporated by reference into the present application.

FIELD OF INVENTION

The invention relates to a drug delivery device, wherein a proximal end of a needle assembly and a distal end of a plunger are configured such that they can get into an adhesion connection.

BACKGROUND

One problem of existing drug delivery devices, which could be, for example, syringes, especially safety syringes, having a retractable needle, is to connect the plunger or the needle assembly so that the needle assembly with the needle could be drawn back into the body unit. The needle assembly and the needle should be drawn back into the body unit so that nobody can be injured by the needle after the use of the drug delivery device.

Some of the drug delivery devices, especially safety syringes having a retractable needle, have a plunger and a needle assembly whereby the plunger and the needle assembly are formed so that they can get into a mechanical connection with each other. They may be formed in a complex way so that if the plunger is pressed onto the needle assembly, the two parts snap into each other like in a key-lock-mechanism.

SUMMARY

One embodiment of the invention is directed to a drug delivery device, comprising: a body unit having a first opening and a second opening, a plunger arranged such that its distal end is positioned inside the body unit, wherein the plunger is moveable in the distal direction with respect to the body unit, a needle assembly, with a proximal end and a distal end comprising a needle, wherein the proximal end of the needle assembly and the distal end of the plunger are configured such that they can get into an adhesion connection.

The drug delivery device which could, for example, be a syringe, preferably a safety syringe, comprises a body unit. This body unit forms a main body of the drug delivery device, which could also be for example a cartridge, an auto-injector or pen-type drug delivery device, and can be formed, for example, in a cylindrical way. The drug delivery device further comprises a plunger which is arranged in a way that its proximal end is positioned outside the body unit and its distal end is positioned inside the body unit. The plunger is movable in the distal direction with respect to the body unit, for example, by pressing on the proximal end of the plunger. The drug delivery device further comprises a needle assembly comprising a needle, wherein the needle comprises an inner surface which forms a channel and an outer surface. The needle assembly has a proximal end and a distal end, wherein the proximal end of the needle assembly is located inside the body unit. The proximal end of the needle assembly and the distal end of the plunger are configured such that they can get into an adhesion connection.

Adhesion is the tendency of certain dissimilar molecules to cling together due to attractive forces. Adhesive materials fill the voids or pores of the surfaces and hold surfaces together by interlocking. For example, two plane surfaces could be connected to each other by adhesive forces if a thin liquid film is formed between these two surfaces.

In another embodiment, the distal end of the plunger has a first connecting element.

In this embodiment, the first connecting element, which could be made of a rigid material, does not change its form when a force impacts on this first connecting element.

In another embodiment, the first connecting element has a first plane connecting surface facing the needle assembly.

In this embodiment, the plunger has a first connecting element at its distal end which comprises a first plane-connecting surface which faces the needle assembly. This first plane-connecting surface is able to get into an adhesion connection with the needle assembly.

In another embodiment, the needle assembly has a second connecting element.

This needle assembly is able to get into a connection by means of the second connecting element with the first connecting element of the plunger.

In another embodiment, the second connecting element has a second plane-connecting surface facing the plunger.

If the plunger also comprises a plane-connecting surface, both parts, the plunger and the needle assembly, could be connected over the two plane connecting surfaces.

In another embodiment, the first and the second plane connecting surfaces are aligned parallel to each other.

If the first and the second plane-connecting surfaces are aligned parallel to each other, these two surfaces are able to get into an adhesion connection. If the two surfaces are aligned parallel to each other, rather than planar, then they may take other geometric forms, for example conical, which increases the surface area of the connecting elements over which the adhesion connection acts, therefore increasing the adhesion force between the first and second connecting elements.

In another embodiment, the first and the second connecting elements, by being pressed on each other, get into an adhesion connection combining the needle assembly with the plunger.

This adhesion connection could be formed over the two plane-connecting surfaces. To form the adhesion connection, the plunger has to be pushed to the needle assembly with only a low force. The two connecting elements do not have to snap into each other, such as is necessary in a key-lock-mechanism, which would require a higher force to be overcome. In contrast, if the two connecting elements form an adhesion connection, the two elements just have to be brought into close proximity.

In another embodiment, there is a thin liquid film between the first and the second connecting surfaces when they get into the adhesion connection.

To get into the adhesion connection in this embodiment, a thin liquid film is formed between the first and the second connection surfaces. Preferably, the first and the second connecting surfaces are plane and arranged parallel to each other. The two connecting surfaces are connected to each other through the interaction forces between each of the connecting surfaces and the thin liquid film.

In another embodiment, the needle assembly is configured to be at least partly drawn back into the body unit, when the plunger is retracted.

The needle assembly is configured in a way, that the resistance of the needle assembly to the retracting force is lower than the force of the adhesion connection.

When the needle assembly with the needle is able to be drawn back into the body unit after the use of the drug delivery device, the risk of injury by needle pricking is reduced. So if the plunger is adhered to the needle assembly, the needle assembly with the needle could be drawn back by means of the plunger into the body unit.

In another embodiment, the drug delivery device is configured such that the needle does not move with respect to the body unit, when the needle assembly gets into the adhesion connection with the plunger.

The needle assembly with the needle should not move with respect to the body unit when the plunger is engaging the needle assembly because of the risk of further advancing the needle into the user's body, which may cause the user pain or discomfort. The needle assembly with the needle could be arranged in the body unit so that it is not able to move in the distal direction.

In one embodiment, the first and the second plane connecting surfaces are made of the same material.

The use of the same material for the first and the second plane connecting surfaces ensures that when the surfaces come into an adhesion contact, for example with a liquid which is positioned between two surfaces, each surface forms an adhesion of the same strength with the liquid. The material for the surfaces could selected in order to form a strong interaction between the surface and the liquid, which could, for example, contain a given drug.

In another embodiment, the first and the second plane-connecting surfaces are made of different materials.

For example, the first plane-connecting surface could be made of the same material as the first connecting element which could also be the same material as the plunger. On the other hand, the second plane connecting surface could be made of the same material as the second connecting surface which could also be the same material as the needle assembly. Forming the plane-connecting surfaces and the connecting elements, and also any other connecting components, for example the plunger or the needle assembly, from the same material reduces the number of production steps and the complexity and cost of the production of the drug delivery device.

In another embodiment, a liquid film is formed between the first plane connecting surface and the second plane connecting surface. The liquid film could engage the two plane connecting surfaces by means of adhesion forces, for example adhesion forces created by surface tension.

In another embodiment, the drug delivery device additionally comprises a chamber located within the body unit and filled with a liquid formulation which may comprise a drug. The first and second connecting elements would therefore each form a seal to the wall of the body unit in order to contain the liquid formulation.

The drug delivery device could be a drug delivery device pre-filled with a medicament, which is made for one use only, or the drug delivery device could also comprise an ampoule or syringe filled with a medicament with retractable needle assembly, which could be replaced after each use of the device.

In another embodiment, the liquid film consists of or contains the drug.

Preferably, the liquid film can be formed out of the drug containing formulation. The liquid film could be formed out of a defined amount of the drug formulation, which stays in the drug delivery device after use.

In another embodiment, the needle unit is not detachable with respect to the body unit, which means that the needle unit and the body unit form one unit together so that the needle assembly could be moved with respect to the body unit. Not detachable also means that the needle assembly and the needle cannot be removed from the body unit and also that a separate needle assembly cannot be attached to the body unit. The drug delivery device could be for example a safety syringe, with a retractable needle.

In another embodiment, wherein the second connecting element is initially located in a position in contact with the inner surface of body unit and is moveable in proximal direction with respect to the body unit to a position where it is no longer in contact with the inner surface of the body unit.

If the body unit has a section with reduced internal diameter in which the second connection element is located in the initial position and the second connection element moves proximally into the body unit it can reach a position where it is no longer in contact with the body unit. The diameter of the second connection element is smaller than that of the main diameter of the body unit. Therefore, once the second connection element has ceased to contact the section of reduced internal diameter, the body unit offers no further resistance to the proximal movement of the second connection element and the needle.

In another embodiment the drug delivery device comprises a medicament. The medicament could be pre-filled in a cartridge or, if the drug delivery device is designed as a syringe, pre-filled in the syringe.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane such as hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

The following figures are for illustrating some embodiments of the drug delivery device.

DETAILED DESCRIPTION

Figure 1:
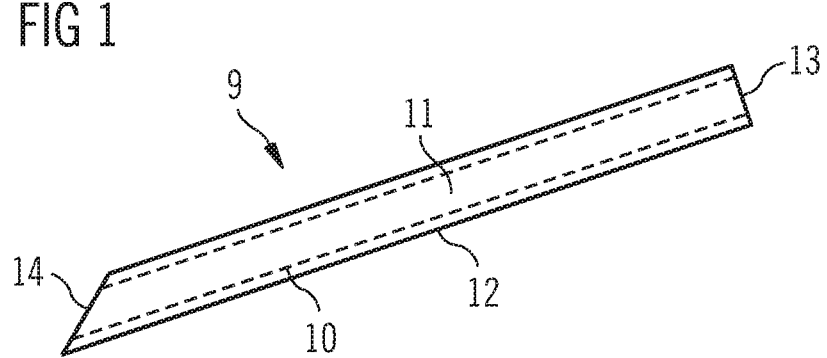
FIG. 1 shows a schematic cross-section of an embodiment of the needle.

FIG. 1 schematically shows the cross-section of an embodiment of the needle 9. The needle 9 comprises an inner surface 10 forming a channel 11 and an outer surface 12. The needle 9, which could be part of a needle assembly, has a proximal end 13 and a distal end 14.

Figure 2:
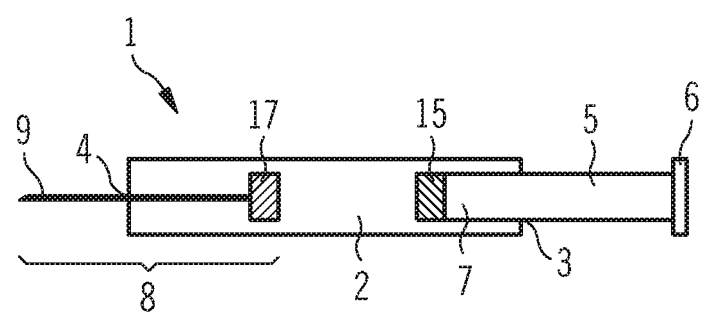
FIG. 2 shows a schematic cross-section of an embodiment of the drug delivery device.

FIG. 2 schematically shows the cross-section of an embodiment of the drug delivery device 1. The drug delivery device 1 comprises a body unit 2 having a first opening 3 and a second opening 4. The drug delivery device 1 further comprises a plunger 5 arranged such that its proximal end 6 is positioned outside of the body unit 2 and its distal end 7 is positioned inside the body unit 2. The plunger 5 is arranged in a way that it is movable in the distal direction with respect to the body unit 2. The drug delivery device 1 further comprises a needle assembly 8 comprising a needle 9 and a second connecting element 17. The plunger 5 comprises a first connecting element 15 located at its distal end 7. The first connecting element 15 and the second connecting element 17 are arranged in a way that they are facing each other.

Figure 3A:
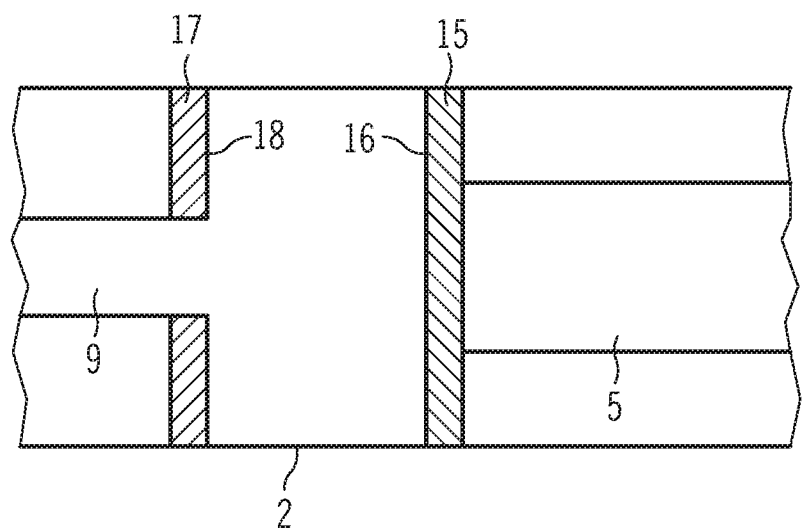
FIGS. 3a/b show a partial view of a schematic cross-section of an embodiment of the drug delivery device.
Figure 3B:
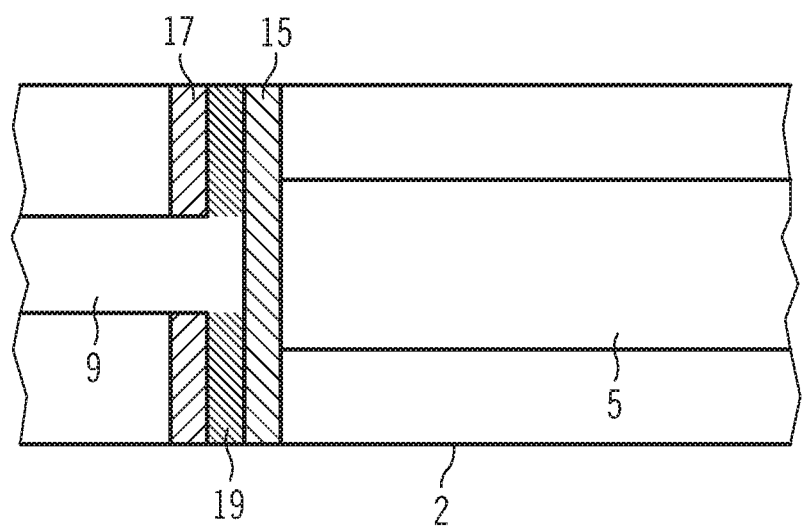

The FIGS. 3a and 3b each show a schematic cross-section of an embodiment of the drug delivery device 1. On the left side of both FIG. 3a/b, there is a section of the needle 9 with the second connecting element 17 and the second connecting surface 18. On the right side of both FIG. 3a/b, the plunger 5 is shown with the first connecting element 15 on its distal end and the first plane-connecting surface 16 on the first connecting element 15. The two connecting surfaces 16, 18 are arranged in a way that they face each other.

In FIG. 3b, the plunger 5 is pushed in the distal direction so far that the first connecting element 15 is now so close to the second connecting element 17 that a thin film 19 is formed between the two connecting elements 15, 17. The two connecting elements 15, 17 are now connected to each other over the adhesion forces between each of the two connecting elements and the liquid film 19.

The FIGS. 4a to 4e show a schematic cross-section of an embodiment of the drug delivery device 1 in five different steps of use.

Figure 4A:
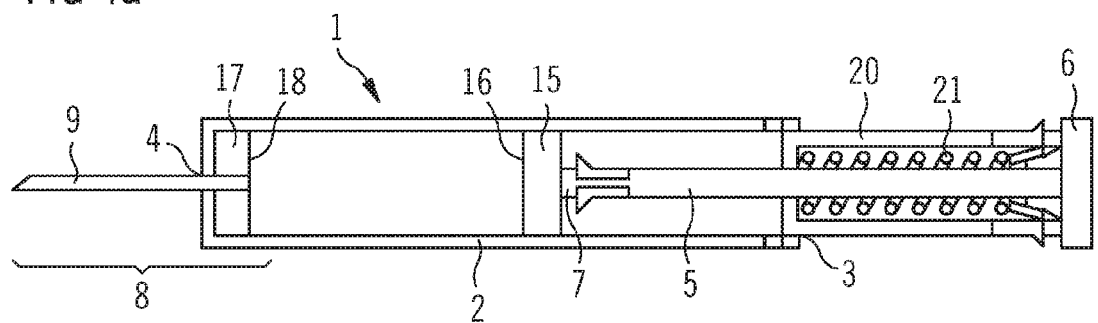
FIGS. 4a-e show a schematic cross-section of an embodiment of the drug delivery device in five different steps of use.

FIG. 4a shows a schematic cross-section of an embodiment of the drug delivery device 1 comprising a body unit 2 with a first opening 3 at the proximal side and a second opening 4 at the distal side. The drug delivery device 1 further comprises a needle assembly 8 comprising a needle 9 and a second connecting element 17 with a second plane connecting surface 18. The drug delivery device 1 further comprises a plunger 5 with a distal end 7 and a proximal end 6. The proximal part of the plunger 5 is surrounded by a sleeve 20. There is a spring 21, which is pre-compressed in a stressed condition, located between the sleeve 20 and the plunger 5. The plunger 5 comprises at its distal end 7 a first connecting element 15 with a first plane-connecting surface 16. A liquid is located between the first connecting element 15 and the second connecting element 17, for example in the case of a pre-filled syringe the liquid could include a drug. FIG. 4a shows the drug delivery device, which could be for example a syringe, preferably a safety syringe, in its starting position.

Figure 4B:
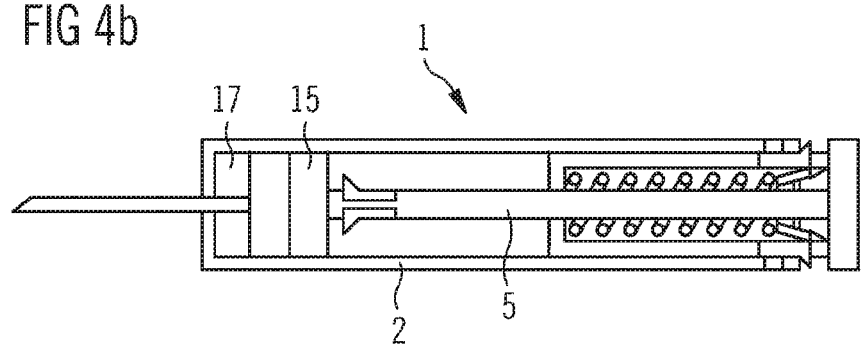

FIG. 4b schematically shows a cross-section of the drug delivery device 1 in an intermediate step of the use of the drug delivery device which is shown in FIG. 4a. In FIG. 4b the plunger 5 is pushed in the distal direction with respect to the body unit 2.

Figure 4C:
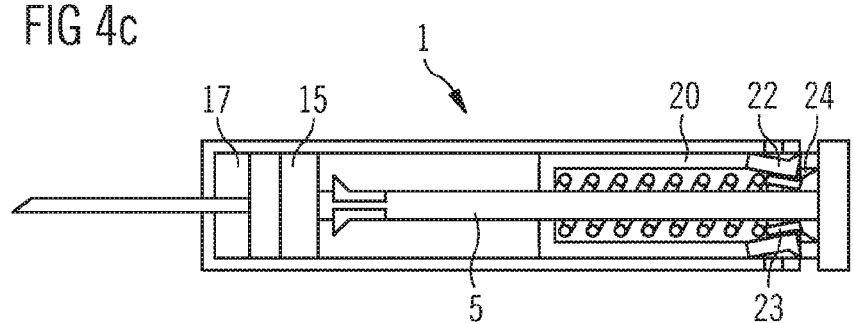

FIG. 4c schematically shows the cross-section of the drug delivery device 1 in an intermediate step of use of the drug delivery device 1 which is shown in FIG. 4a. By further pushing the plunger 5 in the distal direction the snap arms 22 of the sleeve 20 push the plunger rod latch arms 23 inwards. The plunger rod latch arms 23 snap inwards over sleeve latch features 24.

Figure 4D:
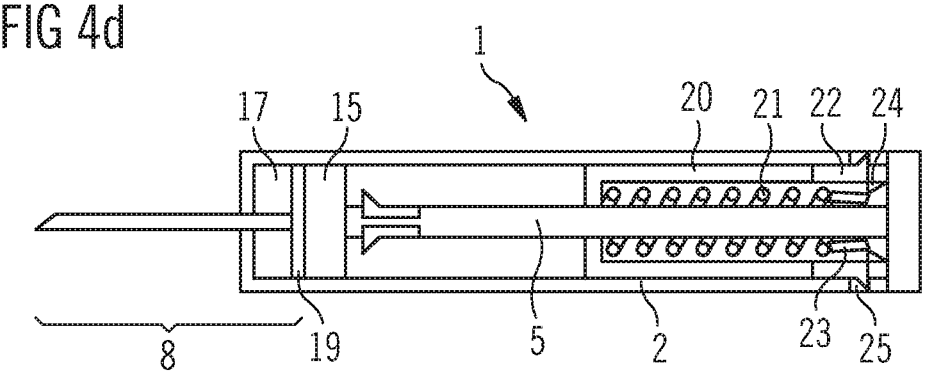

FIG. 4d schematically shows a cross-section of the drug delivery device 1 in an intermediate step of use of the drug delivery device 1 which is shown in FIG. 4a. The first and the second connecting elements 15, 17 have now been pushed so far together that there is only a thin liquid film 19 left between these two connecting elements. Thereby the two connecting elements 15, 17 are able to get into an adhesion connection over the liquid film 19. Thus the plunger 5 and the needle assembly 8 are engaged by an adhesion connection. The sleeve snap arms 22 lock into recesses 25 of the body unit 2. Therefore the sleeve 20 is now connected to the body unit 2 and can no longer move with respect to the body unit 2. The plunger rod latch arms 23 of the plunger 2 remain in their deformed condition clear of the sleeve latch features 24.

Figure 4E:
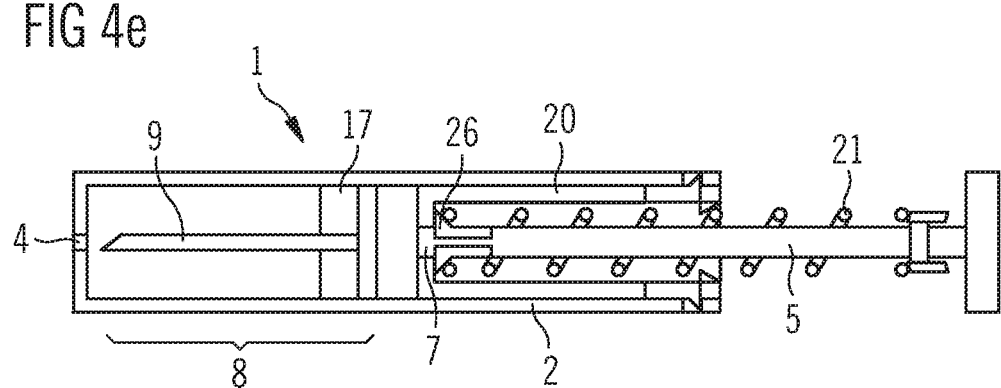

FIG. 4e schematically shows a cross-section of the drug delivery device 1 in a further step of use of the drug delivery device 1 which is shown in FIG. 4a. In FIG. 4e the plunger 5 has been drawn back with respect to the body unit 2 in the proximal direction by the spring 21, which was pre-stressed. The needle 9 has been drawn back so far that the whole needle 9 is located inside the body unit 2. In the end position the distal end 7 has contact to the sleeve 20. The plunger rod snap arms 26 deflect inwards as they pass through a hole in the distal end surface of sleeve 20. Once the plunger rod snap arms 26 are clear of the hole in sleeve 20 the plunger rod snap arms 26 flex outwards to lock the plunger 5 in the rearwards position relative to the sleeve 20 and prevents the needle 9 from moving into the distal direction anymore. Now in the end position the whole needle assembly 8 and the whole needle 9 are located inside the body unit 2. Now the user of the drug delivery device 1 is protected from being injured by the needle 9.

Further embodiments are also possible in which an additional seal is located between the second connecting element 17 and the second opening 4. In this case there are embodiments possible where only the second connecting element 17 and the needle 9 are drawn into the proximal direction and the seal stays in its position.

Figure 5A:
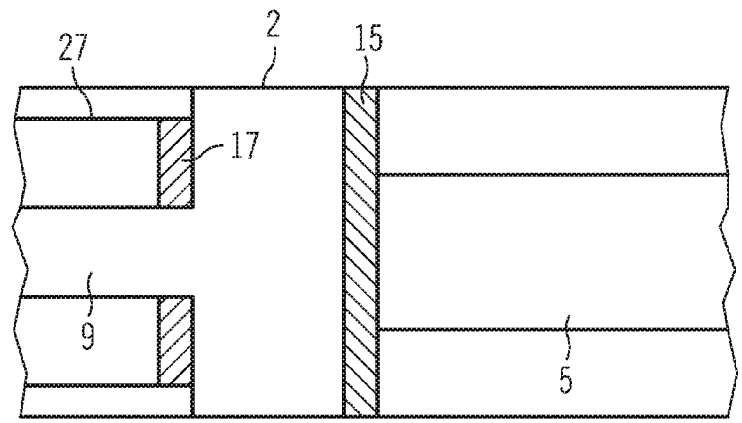
FIGS. 5a-c show a schematic cross-section of another embodiment of the drug delivery device with reduced internal diameter in three different steps of use.
Figure 5B:
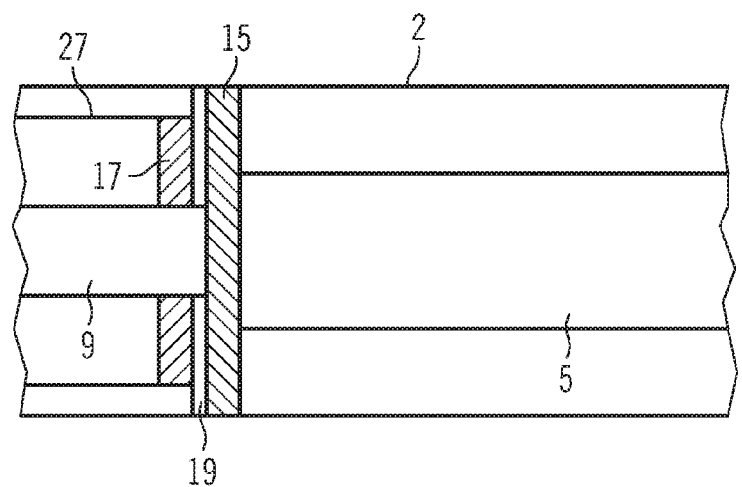
Figure 5C:
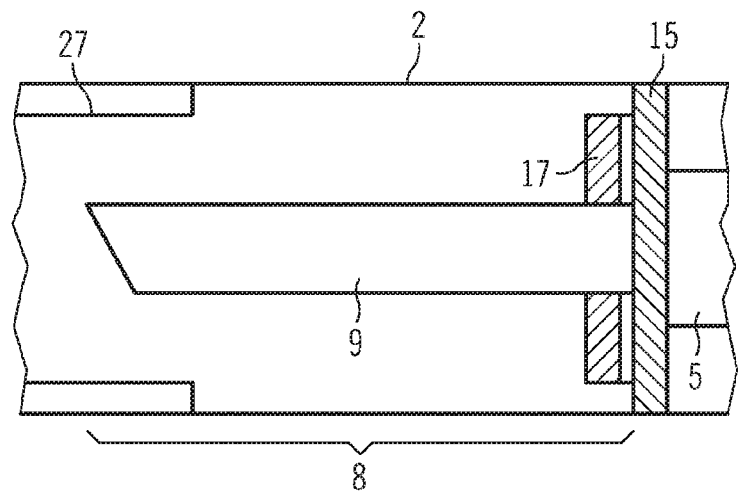

FIGS. 5a-c show a schematic cross-section of an embodiment of the drug delivery device in a section. The three figures show the body unit 2 including a section of reduced internal diameter 27, a section of the needle 9 on the left side and a section of the plunger 5 on the right side. The second connecting element 17, which is located at the proximal end of the needle 9, is shown. The second connecting element 17 is formed planar in this embodiment. The second connecting element 17 is formed with a smaller diameter compared to both the diameter of the first connecting element 15 and to the main internal diameter of the body unit 2. The proximal end of needle 9 aligns with the second connecting element 17. FIG. 5a shows the shows the drug delivery device 1, which could be for example a syringe, preferably a safety syringe, in its starting position.

The FIG. 5b shows the situation when then plunger 5 is moved to the distal direction with respect to the body unit 2.

The plunger 5 is pushed in the distal direction so far that the first connecting element 15 is now so close to the second connecting element 17 that a thin film 19 is formed between the two connecting elements 15, 17. The two connecting elements 15, 17 are now connected to each other over the adhesion forces between each of the two connecting elements and the liquid film 19.

The FIG. 5c shows the situation when then plunger 5 is moved to the proximal direction with respect to the body unit 2. The adhesion connection causes the needle assembly 8 of needle 9 and second connection element 17 to move in the proximal direction drawing the needle into the body unit 2. As the second connection element 17 moves proximally into the body unit 2 quickly reaches a position where it is no longer in contact with the section of the body unit 2 with reduced internal diameter 27. The diameter of the second connection element 17 is smaller than that of the main diameter of the body unit 2. Therefore, once the second connection element has ceased to contact the section of reduced internal diameter 27, the body unit 2 offers no further resistance to the proximal movement of the second connection element 17 and the needle 9. This offers a significant advantage compared, for example, to the embodiment shown in FIG. 3a/b, that the force required to draw the needle 9 into the body unit 2 is greatly reduced. A further advantage of this reduction in force is that there is now no force working against the adhesion connection between the first and second connecting elements 15,17. This significantly reduces the risk that the adhesion connection will fail.

The invention claimed is:

1. A drug delivery device, comprising:
a body unit having a first opening and a second opening;
a plunger arranged such that its distal end is positioned inside the body unit, wherein the plunger is moveable in the distal direction with respect to the body unit; and
a needle assembly, with a proximal end and a distal end comprising a needle, where the needle assembly is retained within the body unit by a resistance force;
wherein the proximal end of the needle assembly and the distal end of the plunger are configured to form an adhesion connection that generates an adhesion force that is greater than the resistance force.

2. A drug delivery device according to claim 1, wherein the distal end of the plunger has a first connecting element.

3. A drug delivery device according to claim 2, wherein the first connecting element has a first plane connecting surface facing the needle assembly.

4. A drug delivery device according to claim 1, wherein the needle assembly has a second connecting element.

5. A drug delivery device according to claim 4, wherein the second connecting element has a second plane connecting surface facing the plunger.

6. A drug delivery device according to claim 5, wherein the first and the second plane connecting surface are aligned parallel to each other.

7. A drug delivery device according to claim 5, wherein, by being pressed on each other, the first and the second connecting element get into a adhesion connection combining the needle assembly with the plunger.

8. A drug delivery device according to claim 7, wherein there is a thin liquid film between the first and the second connecting surface, when they get into the adhesion connection.

9. A drug delivery device according to claim 7, wherein the needle assembly is configured to be at least partly drawn back into the body unit, when the plunger is retracted after the adhesion connection is formed and the adhesion force becomes greater than the resistance force.

10. A drug delivery device according to claim 7, wherein the drug delivery device is configured such that the needle does not move with respect to the body unit, when the needle assembly gets into the adhesion connection with the plunger.

11. A drug delivery device according to claim 5, wherein the first and the second plane-connecting surfaces are made of the same material.

12. A drug delivery device according to claim 5, wherein a liquid film is formed between the first plane connecting surface and the second plane connecting surface.

13. A drug delivery device according to claim 1, additionally comprising a chamber located within the body unit and filled with a drug.

14. A drug delivery device according to claim 1, wherein the needle assembly is not detachable with respect to the body unit.

15. A drug delivery device according to claim 1, wherein the second connecting element is initially located in a position in contact with the inner surface of body unit and is moveable in proximal direction with respect to the body unit to a position where it is no longer in contact with the inner surface of the body unit.

16. A drug delivery device according to claim 1, wherein the device is pre-filled with a medicament.

17. The drug delivery device of claim 1 wherein the adhesion connection is the only type of connection between the proximal end of the needle assembly and the distal end of the plunger.

* * * * *

UNITED STATES PATENT AND TRADEMARK OFFICE
CERTIFICATE OF CORRECTION

PATENT NO. : 8,702,659 B2
APPLICATION NO. : 13/202440
DATED : April 22, 2014
INVENTOR(S) : Lanin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 73 days.

Signed and Sealed this
Twenty-ninth Day of September, 2015

Michelle K. Lee
*Director of the United States Patent and Trademark Office*